US011250715B1

(12) United States Patent
Francis et al.

(10) Patent No.: US 11,250,715 B1
(45) Date of Patent: Feb. 15, 2022

(54) COMPUTING SYSTEM FOR PRESENTING TRAINING DATA WITHIN AN ELECTRONIC HEALTH RECORD APPLICATION

(71) Applicant: Allscripts Software, LLC, Raleigh, NC (US)

(72) Inventors: Sabrina Francis, Raleigh, NC (US); Simon Levy, Raleigh, NC (US); Bonnie Bordeaux, Raleigh, NC (US); Vishwajit Menon, Pune (IN)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 591 days.

(21) Appl. No.: 15/994,632

(22) Filed: May 31, 2018

(51) Int. Cl.
  *G09B 5/06* (2006.01)
  *G16H 10/60* (2018.01)
(52) U.S. Cl.
  CPC ............ *G09B 5/065* (2013.01); *G16H 10/60* (2018.01)
(58) Field of Classification Search
  CPC .......... G09B 5/065; G09B 5/06; G09B 19/00; G16H 10/60
  See application file for complete search history.

(56) References Cited

U.S. PATENT DOCUMENTS

| | | | |
|---|---|---|---|
| 4,622,013 A | 11/1986 | Cerchio | |
| 5,602,982 A | 2/1997 | Judd et al. | |
| 5,791,907 A | 8/1998 | Ramshaw et al. | |
| 6,283,761 B1 | 9/2001 | Joao | |
| 7,201,580 B2 * | 4/2007 | Ho | G09B 7/04 434/118 |
| 2002/0016923 A1 | 2/2002 | Knaus et al. | |

* cited by examiner

*Primary Examiner* — Timothy A Musselman
(74) *Attorney, Agent, or Firm* — Medley, Behrens & Lewis, LLC

(57) ABSTRACT

Described herein are various technologies pertaining to presenting training data for a task performed using an electronic health records application (EHR) to healthcare workers. A context for a task to be performed within the EHR is transmitted to a server from a client EHR. The context includes data indicative of or pertaining to a healthcare worker using the client EHR, an element of a graphical user interface (GUI) of the client EHR, or other data indicative of the task to be performed within the EHR. The server transmits a list of training materials to the client EHR based upon the context, where the training materials comprise data pertaining to performance of one or more tasks by way of the client EHR. Responsive to receiving the list, the client EHR displays an indication of a training material in the training materials within the GUI of the client EHR.

20 Claims, 8 Drawing Sheets ns on how to perform a task within the EHR. The training application can then transmit the list to the client computing device for presentation in a graphical user interface (GUI) for the training application on the display of the client computing device, where the GUI for the training application can be displayed concurrently with a GUI for the EHR. Thus, in contrast with conventional approaches to providing training materials to users of an EHR, the EHR and training application systems described herein facilitate presentment of training materials to a healthcare worker using the EHR without requiring navigation away from the EHR interface.

COMPUTING SYSTEM FOR PRESENTING TRAINING DATA WITHIN AN ELECTRONIC HEALTH RECORD APPLICATION

BACKGROUND

Electronic health record applications (EHRs) are robust applications that are utilized in medical facilities across a variety of aspects of a medical practice. EHRs are configured with functionality pertaining to patient intake, patient billing, insurance billing, prescription generation, maintaining a record of patient care over time, etc. EHRs are often used by healthcare workers at the point of care (i.e., at a time when the healthcare worker is providing care to a patient). For example, a healthcare worker may retrieve data from a patient record maintained by an EHR to relatively quickly ascertain problems being experienced by the patient, medications currently being taken by the patient, and so forth.

Despite the prevalence of EHRs in healthcare environments, many healthcare workers find EHRs difficult to use. Moreover, EHRs receive frequent version updates, which can sometimes modify the functionality of the EHR and/or the steps required to perform certain tasks within the EHR. Often, this will require a healthcare worker to exit or navigate away from an EHR client interface in order to perform an Internet search to determine how to perform a given task in the EHR. Other times, the healthcare worker will be forced to contact a service department of the provider of the EHR in order to determine how to perform a task. This results in lost productivity for the healthcare worker and the healthcare organization, as well as the provider of the EHR.

SUMMARY

The following is a brief summary of subject matter that is described in greater detail herein. This summary is not intended to be limiting as to the scope of the claims.

Described herein are various technologies pertaining to presenting training data to healthcare workers within an interface of an electronic health records application (EHR). More specifically, a computer-executable training application running on a server computing device is described herein, wherein the training application may be configured to execute alongside an EHR (or a supplement application to the EHR) and is configured to present training materials to a healthcare worker within an interface of the EHR. In general, a training material comprises instructions on how to perform a task using the EHR, such as issuing an electronic prescription for a patient. In exemplary embodiments, the training material may be a text-based document, an audio file, a video file, and/or an interactive tutorial.

By way of example, a healthcare worker may be utilizing an EHR on a client computing device and may decide that he or she requires instruction on how to perform a task using the EHR. In an exemplary embodiment, the client computing device can receive input from the healthcare worker which causes the client computing device to capture a context for the EHR. For example, the context can include at least one of an identifier for a clinical activity, an identifier for a specific GUI element within the EHR, an identifier for the healthcare worker, and an indication of job function of the healthcare worker. The client computing device can then transmit this context to the training application executing on the server computing device. Responsive to receiving the context, the training application can generate a list of training materials based upon the context, each training material in the list of training materials comprising instruc- The healthcare worker can review the list of training materials and decide that he or she wishes to access a first training material. The client computing device can receive input indicating that the healthcare worker wishes to access the first training material. Responsive to receiving the input, the client computing device can transmit an identifier for the first training material to the training application. Responsive to receiving the identifier for the first training material, the training application can retrieve the first training material and transmit the first training material to the client computing device for presentation on the display of the client computing device. The training application may also be configured to recommend certain training materials to the healthcare worker and to identify newly added training materials.

The systems and methods described herein provide various advantages over conventional systems for providing training materials pertaining to an EHR application. First, the training application provides convenient access to training materials within an interface of the EHR, such that training materials can be accessed by a healthcare worker using the EHR without navigating away from the EHR interface. This enables a healthcare worker to determine how to perform a task using an EHR more efficiently when compared with conventional approaches to software use training. Furthermore, the systems and methods described herein facilitate provision of training materials based upon context of the EHR in operation by the healthcare worker, thereby facilitating presentment of training materials that are relevant to a task that is desirably performed within the EHR interface. Additionally, by providing training materials in a variety of formats (e.g., written, visual, audio, interactive, etc.), the training application allows a healthcare worker to use his or her preferred learning medium. Still further, by providing recommendations and highlighting newly added training materials, the training application can keep a healthcare worker up to date with the most relevant information.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
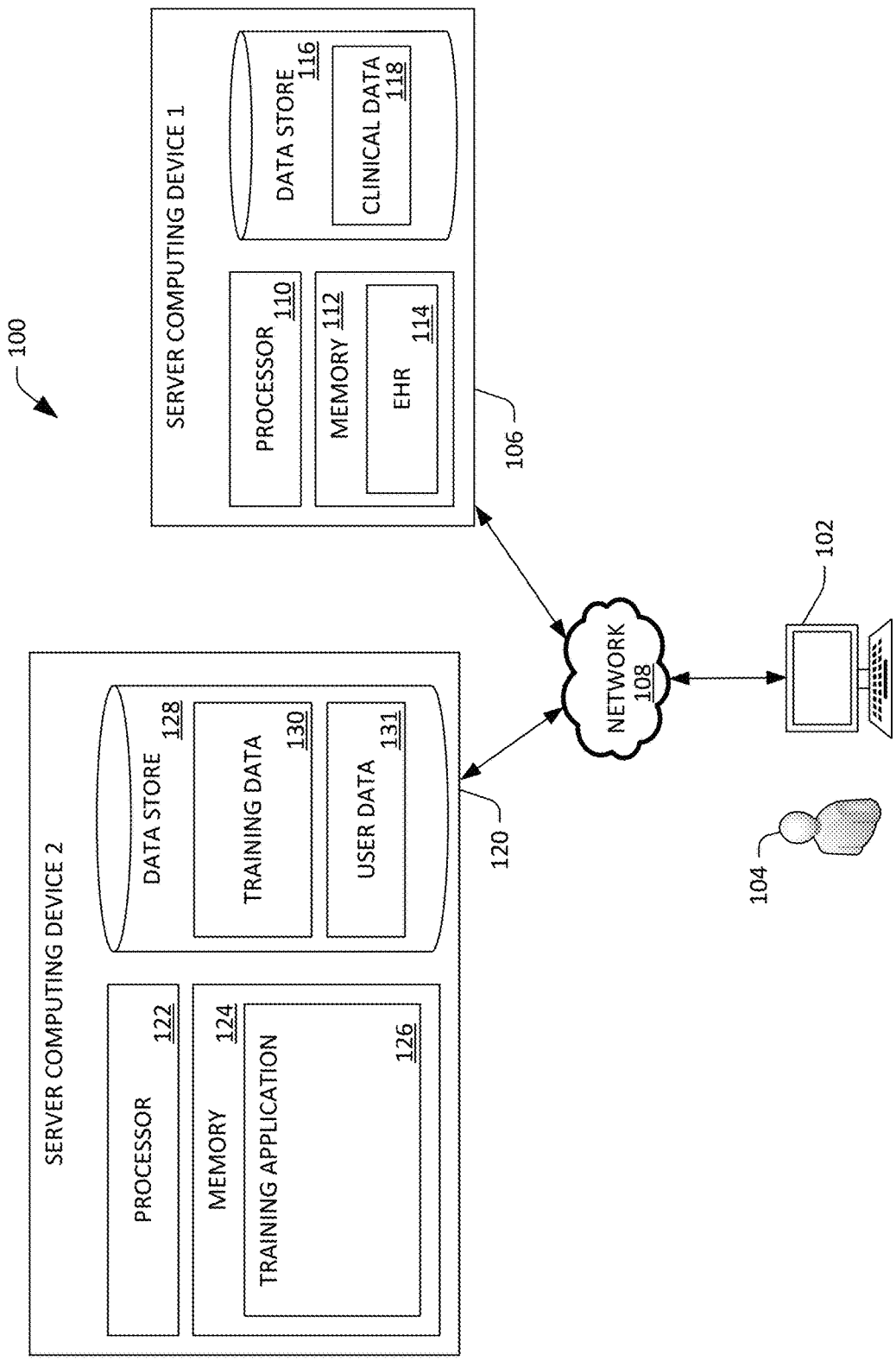
FIG. 1 is a functional block diagram of an exemplary system that facilitates presenting training material pertaining to a task performed in an electronic health records application (EHR) to a healthcare worker.

Various technologies pertaining to presenting training data to healthcare workers are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary system 100 that facilitates presenting training data to a healthcare worker is illustrated. The system 100 includes a client computing device 102 that is operated by a healthcare worker 104 in a healthcare environment (e.g., a hospital, a primary care provider's office, an urgent care facility, etc.). The client computing device 102 may be any suitable type of computing device including, but not limited to, a laptop computing device, a tablet computing device, a mobile telephone, a wearable computing device (e.g., a watch, eyewear etc.), a kiosk, etc. The client computing device 102 comprises a processor 132 and memory 134 that comprises instructions that are executed by the processor 132. The memory 134 has a client electronic health record application (EHR) 136 loaded therein, as well as a client training application 138, which are tasked with interacting with the server EHR 114 and the training application 126, respectively. In general, it is contemplated that the client computing device 102 receives input from the healthcare worker 104 during the course of providing treatment to a patient and the client EHR application will use this input to perform a healthcare related task (e.g. generating a prescription for a patient, updating a patient record, etc.). Furthermore, it is contemplated that the client training application will present training data to the healthcare worker related to the functionality of the EHR. As such, the client computing device 102 further comprises a display 140 on which is displayed a graphical user interface 142. The client computing device 102 can display or receive data pertaining to either of the client EHR 136 or the client training application 138 by way of the GUI 142.

The system 100 further includes a first server computing device 106 that is in network communication with the client computing device 102 by way of a network 108 (e.g., Internet, intranet, etc.). The first server computing device 106 comprises a processor 110 and memory 112, wherein the memory 112 has a server EHR 114 loaded therein, wherein the server EHR 114 is executed by the processor 110. The server EHR 114 is configured to perform a variety of tasks related to patient care in a healthcare facility (e.g., patient intake, prescription generation, patient record creation and maintenance, etc.). The first server computing device 106 also includes a data store 116 that comprises clinical data 118 about patients, wherein the clinical data 118 is maintained by the server EHR 114. The clinical data 118 can include electronic health records, claims data, patient/disease registries data, health surveys data, and/or clinical trials data.

For instance, electronic health records include, but are not limited to including, administrative and demographic information, diagnosis, treatment, prescription drugs, laboratory tests, physiological monitoring data, hospitalization, patient insurance, etc. Administrative information includes hospital discharge data (e.g., reported to a government agency). Claims data describes billable interactions (insurance claims) between insured patients and the healthcare delivery system, and can include four general categories: 1) inpatient; 2) outpatient; 3) pharmacy; and 4) enrollment. Patient/disease registries data includes data generated by clinical information systems that track data for certain chronic conditions, such as Alzheimer's Disease, cancer, diabetes, heart disease, and asthma. Health surveys data includes data from national surveys pertaining to common chronic conditions. Clinical trials data includes data generated during conductions of clinical trials.

Additionally, the system 100 includes a second server computing device 120 that is in network communication with the client computing device 102 and the first server computing device 106 by way of the network 108. The second server computing device 120 comprises a processor 122 and memory 124, wherein the memory 124 has a training application 126 loaded therein, and further wherein the processor 122 executes the training application 126. In general, the training application 126 is configured to provide training data to the client computing device 102 for presentment to a healthcare worker using the client computing device 102. The second server computing device 120 further includes a data store 128 comprising training data 130 and user data 131. In general, the training data 130 includes a plurality of training materials, wherein each training material in the plurality of training materials comprises instructions on how to perform a specific task by way of the client EHR 136. In a non-limiting example, the training data 130 may include text-based files, audio files, video files, interactive tutorials, etc. By way of example, a training material may be a video file demonstrating performance of a task using the client EHR 136 by way of interaction with the GUI 142. In another example, a training material may be a text-based file that includes text describing how to perform a task using the client EHR 136. In still another example, a training material may be an audio file comprising narrated instructions pertaining to performance of a task by way of the client EHR 136.

The training data 130 may also include a plurality of ratings each corresponding to a particular training material in the plurality of training materials, wherein the ratings are indicative of how useful other healthcare workers found each training material in the plurality of training materials. Furthermore, the training data 130 may include tags for each training material, wherein the tags for a training material are indicative of the content of the media example. For example, a training material pertaining to issuance of electronic prescriptions by way of the client EHR 136 can include the tag "prescriptions." Additionally, the training data 130 may include an upload datetime for each training material. It is contemplated that the second server computing device 120 will receive new training materials from different sources from time to time and that the second server computing device 120 will store the new training materials in the data store 128. The training application 126 can further be configured to remove outdated training materials in the training data 130. The user data 131 comprises data relating to users of the training application 126, such as the healthcare worker 104.

Exemplary operation of the system 100 is now set forth. The client computing device 102 receives user credentials from the healthcare worker 104 and transmits the user credentials to the first server computing device 106 for authentication. The server EHR 114 authenticates the healthcare worker 104 and provides the healthcare worker 104 with access to the functionality of the server EHR 114 via the client EHR 136 executing on the client computing device 102. It is contemplated that the healthcare worker 104 is operating the client EHR 136 on the client computing device 102. Furthermore, it is contemplated that the healthcare worker 104 wishes to receive instructions on how to perform a given task related to patient care (e.g., generating an electronic prescription) using the client EHR 136. The client computing device 102 receives first input from the healthcare worker 104 by way of the GUI 142, the first input indicative of a desire to access a training material pertaining to a task that is desirably performed using the client EHR 136, as will be explained in greater detail below. Responsive to receiving the first input at the client computing device 102, the client EHR 136 transmits a context to the training application 126 of the second server computing device 120, the context usable by the training application 126 to identify training materials pertinent to the task desirably performed by the healthcare worker 104 using the client EHR 136. The client computing device 102 can further receive second input from the healthcare worker 104 that is indicative of the particular task desirably performed using the client EHR 136. In a nonlimiting example, the context may include the second input from the healthcare worker that is indicative of the task desirably performed using the client EHR 136 and/or data that is indicative of at least one of an identifier for a clinical activity, an identifier for a specific GUI element within the client EHR, an identifier for the healthcare worker 104, and a job function of the healthcare worker 104. Responsive to receiving the first input from the healthcare worker 104, the client computing device 102 transmits the context via the network 108 to the second server computing device 120 executing the training application 126. In an embodiment, the client computing device 102 can generate a first application programming interface (API) call comprising the context. By way of example, the first API call can be an HTTP/s request.

Accordingly, the second server computing device 120 receives the context from the client computing device 102. In an embodiment, the second server computing device 120 can detect the first API call by monitoring a first port for the first HTTP/s request. In an embodiment, the training application 126 may determine whether the healthcare worker 104 and/or the healthcare organization to which the healthcare worker 104 belongs has subscribed to the services provided by the training application 126 based upon the context. For example, in an embodiment wherein the context comprises an identifier of the healthcare worker 104, the training application 126 can determine that the healthcare worker 104 is authorized to use services provided by the training application based upon the identifier of the healthcare worker 104. When the training application 126 determines that the healthcare worker 104 and/or the healthcare organization of the healthcare worker 104 has not subscribed to the services of the training application 126, the training application 126 may transmit a message to the client computing device 102 indicating that the services provided by the training application 126 are not available to the healthcare worker 104 and/or the healthcare organization of the healthcare worker 104. The message may also include instructions on how to obtain the services provided by the training application 126.

When the training application 126 has determined that the healthcare worker 104 has access to the services provided by the training application 126, and responsive to receiving the context from the client computing device 102, the training application 126 generates a list of training materials for the task by executing a search over the training data 130 stored in the data store 128 based on the data contained in the context. Each training material in the list of training materials comprises instructions on how to accomplish a task using the client EHR 136. The list of training materials may comprise a plurality of text-based documents, a plurality of audio files, a plurality of video files, a plurality of interactive tutorials, etc. For example, when the context indicates that instruction on how to generate an electronic prescription using the server EHR 114 is requested (e.g., as indicated in data input by the healthcare worker 104 to the client computing device 102 by way of the client EHR 136), the training application 126 can identify training materials in the training data 130 stored in the data store 128 that are tagged with "electronic prescription" and include such materials in the list of training materials.

Responsive to generating the list of training materials, the training application 126 transmits data to the client computing device 102 which causes the client computing device 102 to present the list of training materials in the GUI 142. In an exemplary embodiment, the list of training materials may be presented in the GUI 142 simultaneously with a GUI of the client EHR 136 on the display 140 of the client computing device 102. In various embodiments, the list of training materials is presented in the GUI 142 as part of a GUI of the client EHR 136. In another embodiment, the list of training materials may be displayed in a separate window.

The healthcare worker 104 may then examine each training material in the list of training materials, and in an example, may decide that he or she wishes to access a first training material in the list of training materials. The client computing device 102 receives input from the healthcare worker 104 indicating that the healthcare worker wishes to access the first training material. Responsive to receiving the input, the client computing device 102 can transmit, by way of the network 108, an identifier for the first training material to the second server computing device 120 executing the training application 126. In an embodiment, the identifier for the first training material can be transmitted via a second API call generated by the client computing device 102, wherein the second API call is an HTTP/s request.

The second server computing device 120 can then receive the identifier for the first training material. In an embodiment, the second server computing device 120 can detect the second API call by monitoring a second port for the HTTP/s request. Responsive to receiving the identifier for the first training material, the training application 126 may retrieve the first training material by executing a search over the training data 130 based on the identifier for the first training material. In an embodiment, the training application 126 can also record (e.g., in the training data 130 or the user data 131) that the first training material has been accessed by the healthcare worker 104. The training application 126 can record this information for a plurality of healthcare workers so as to store a total view count for the first training material. The training application 126 may then transmit the first training material to the client computing device 102 for presentation on the display 140 of the client computing device 102. In an embodiment, the first training material is a video file and is "streamed" to the client computing device 102. In another embodiment, the first training material is a text-based document and is transmitted in its entirety to the client computing device 102 where it can be viewed by the healthcare worker 104.

In an embodiment, after reviewing the first training material, the healthcare worker 104 may assign a rating indicative of how useful the first training material was in preparing him or her to complete the task using the server EHR 114. The client computing device 102 can receive input from the healthcare worker 104 that is indicative of the rating and can transmit the input to the second server computing device 120. The second server computing device 120 can then associate the rating with the first training material in the training data 130. The training application 126 may repeat this process a plurality of times for a plurality of training materials such that each training material in the training data 130 has an associated average rating. In an exemplary embodiment, the training application 126 can be configured to provide training materials having a rating higher than a certain threshold to the client training application 138 responsive to receiving the context from the client computing device 102. In another exemplary embodiment, the client training application 138 can be configured to present training materials in a ranked fashion in the GUI 142 such that training materials having a higher average rating are presented preferentially (e.g., above training materials having a lower average rating, prior to displaying training materials having a lower average rating, etc.).

The training application 126 may also present training materials for tasks based upon recommendations. In an embodiment, an administrator of the server EHR 114 (e.g. an information technology worker) may identify certain training materials that may be of interest to the healthcare worker (or a group of healthcare workers). For example, if a particular functionality of the server EHR 114 has been altered through a version update, the administrator may identify a recommended training material explaining the altered functionality. In an example, the server EHR 114 can communicate an indication of a recommended training material to the second server computing device 120 by way of the network 108. Responsive to receipt of the indication, the training application 126 can update the training data 130 and/or the user data 131 with data that indicates that a training material is recommended to the healthcare worker 104 and/or the organization to which the healthcare worker 104 belongs (e.g., a medical practice). Subsequently, responsive to receipt by the second server computing device 120 of context comprising an identifier of the healthcare worker 104, the training application 126 can transmit the recommended training material to the client training application 138. When the GUI for the client training application 138 is presented on the display 140 of the client computing device 102, an indication of the recommended training material may be presented in the GUI 142. The training application 126 can also be configured to receive a notification from the client computing device 102 that the recommended training material has been presented to the healthcare worker 104 on the client computing device 102. The training application 126 can forward this notification to an administrator computing device (not shown, e.g., by way of which a recommendation was input by the administrator) so as to inform the administrator that the healthcare worker 104 has viewed the training material.

In another embodiment, an upload datetime is associated with each training material when it is stored in the data store 128. Furthermore, the training application 126 can be configured to record the current datetime whenever the training application 126 receives a context that is indicative of the healthcare worker 104 from the client computing device 102. By way of example, the client training application 138 can be configured to include an identifier of the healthcare worker 104 when the healthcare worker 104 is logged into the client EHR 136. When the training application 126 subsequently receives a context that is indicative of the healthcare worker 104, the training application 126 can conduct a search over the training data 130 for training materials that have been uploaded since the last context indicative of the healthcare worker 104 was received by the training application 126. The training application 126 can then provide training materials to the client training application 138 that have been added to the data store 128 since the last time a context indicative of the healthcare worker 104 was received at the second server computing device 120.

The system 100 provides various advantages over conventional training systems for EHRs. The system 100 provides fast, convenient access to a wide variety of training materials within an interface of a client EHR 136 such that the healthcare worker 104 does not lose his or her place within a workflow of the client EHR 136 by having to navigate away from the interface of the client EHR 136 to access a training material. This enables the healthcare worker 104 to determine how to perform a task using the server EHR 114 more efficiently when compared with conventional approaches to software use training. Furthermore, by providing training materials in a variety of formats (e.g., written, visual, audio, interactive, etc.), the training application 126 allows the healthcare worker 104 to use his or her preferred learning format. Third, by providing recommendations and highlighting newly added training materials, the training application 126 can keep the healthcare worker up to date with the most relevant information, leading to increased productivity.

Figure 2:
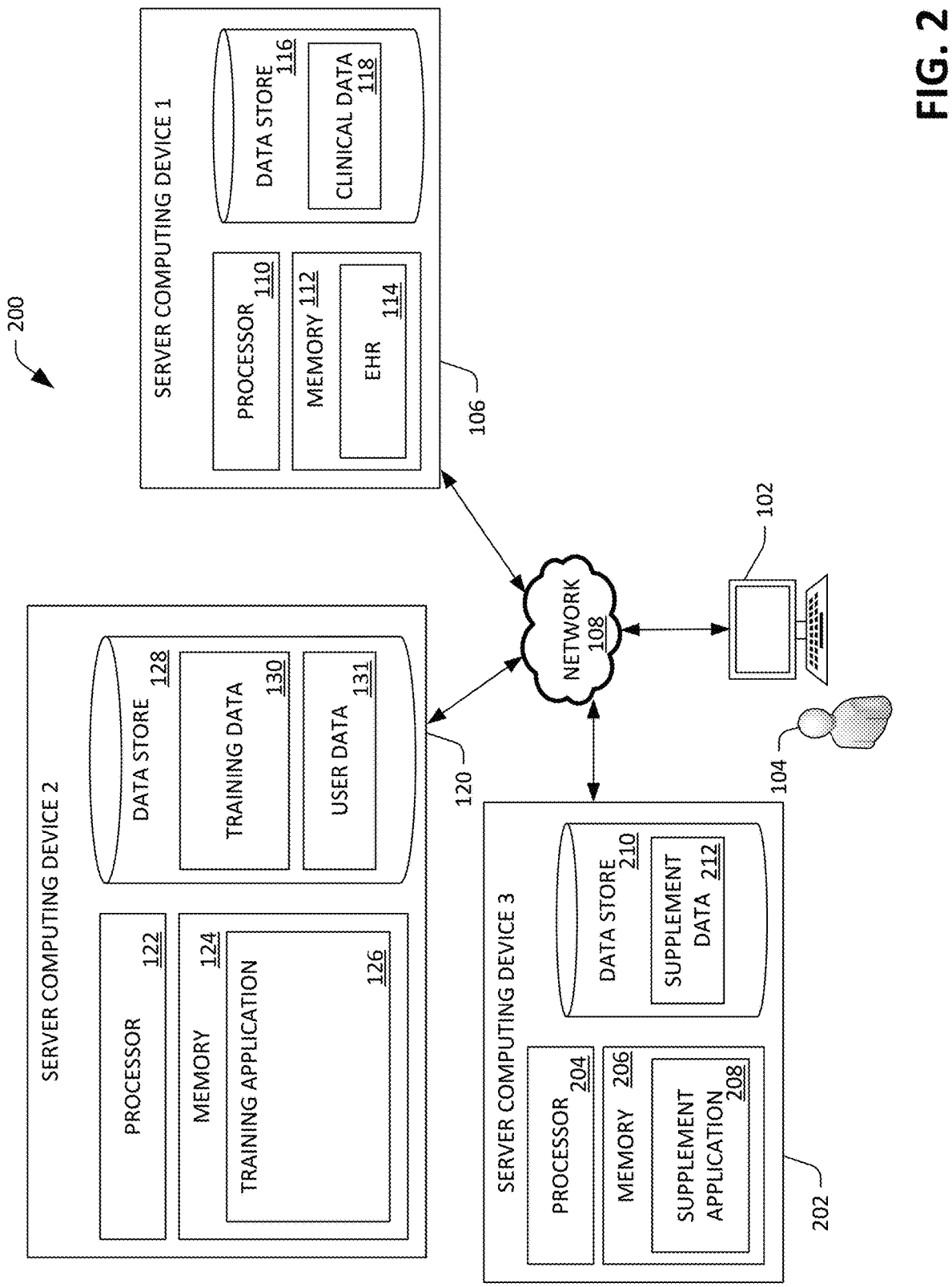
FIG. 2 is a functional block diagram of an exemplary system that facilitates presenting training material for a task performed in a supplement application to a healthcare worker.

Referring now to FIG. 2, an exemplary system 200 that facilitates presenting training material for a task performed using a supplement application to an EHR is illustrated. A supplement application is an application that provides functionality not normally provided by an EHR. The system 200 includes the client computing device 102, the first server computing device 106, and the second server computing device 120, as well as their respective components depicted in FIG. 1.

The system 200 additionally comprises a third server computing device 202 in network communication with the client computing device 102, the first server computing device 106, and the second server computing device 120. The third server computing device 202 comprises a processor 204 and memory 206, wherein the memory 206 has a supplement application 208 loaded therein. When executed by the processor 204, the supplement application 208 is configured to provide functionality not traditionally provided by the server EHR 114. The memory 134 of the client computing device 102 may include a client supplement application 209 configured to interface with the supplement application 208 executing on the third server computing device 202. The third server computing device 202 may also optionally comprise a data store 210 storing supplement data 212 used by the supplement application 208, the supplement data 212 comprising various data pertaining to a plurality of patients. For example, the supplement data 212 can include data that may be relevant to providing healthcare to a patient, but that is not input to or stored by the server EHR 114. It is understood there may be overlap between the supplement data 212 and the clinical data 118.

The system 200 operates in a similar fashion to the system 100 described in FIG. 1 above, except that the training application 126 and client training application 138 further operate to present training data pertaining to tasks performed using the client supplement application 209. More specifically, the second server computing device 120 can receive a context for a task performed using the client supplement application 209. Similar to exemplary embodiments described above, the context can be or include at least one of an identifier for the task, an identifier for a specific GUI element within the client supplement application, an identifier for the healthcare worker 104, and a job function of the healthcare worker 104. Thus, the client training application 138 can be configured to present training materials pertaining to tasks performed by way of the client supplement application 209 based upon a context of the client supplement application 209. Responsive to receiving the context from the client computing device 102, the training application 126 can generate a list of training materials by executing a search over the training data 130 based on data contained in the context. The training application 126 can then transmit data to the client computing device 102 that causes the list of training materials to be presented in the GUI 142. When the healthcare worker 104 selects a first training material in the list of training materials, the client training application 138 transmits an indication of the selection to the training application 126. Responsive to receiving the indication of the selection, the training application 126 transmits data that causes the first training material to be presented to the healthcare worker 104 on the client computing device 102.

Figure 3:
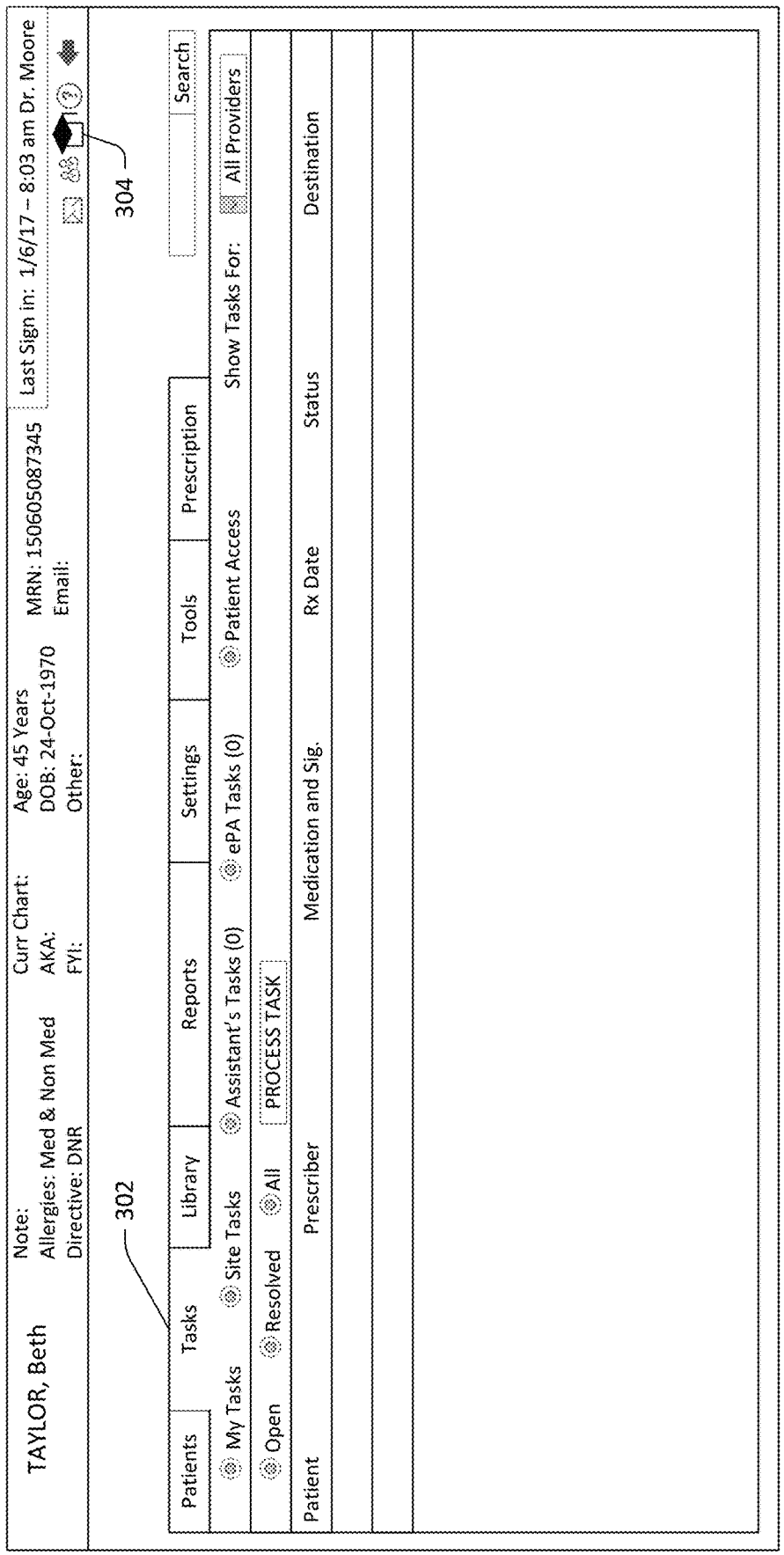
FIG. 3 is an exemplary graphical user interface (GUI) for an EHR.

Turning now to FIG. 3, an exemplary GUI 300 that can be presented on the display 140 of the client computing device 102 is depicted. As noted above, the healthcare worker 104 can be authenticated by the server EHR 114. For instance, the server EHR 114 can receive credentials of the healthcare worker 104 that are input to the client computing device 102 by the healthcare worker 104 by way of the client EHR 136, and the server EHR 114 can cause graphical data to be presented on the display 140 of the client computing device 102 based upon the received credentials. The server EHR 114 can also receive data that identifies a patient from the client computing device 102 (e.g., as provided by the healthcare worker 104), and the server EHR 114 can return information about the patient to the client computing device 102 (such as at least a portion of the medical record of the patient).

The GUI 300 can include a region 302 that illustrates clinical data pertaining to the patient as maintained by the server EHR 114. The GUI 300 also includes a selectable graphical indicia 304, wherein the client training application 138 can cause the graphical indicia 304 to be presented on the display 140 of the client computing device 102 (e.g., as a selectable overlay). The graphical indicia 304 can be selected by a healthcare worker 104. Responsive to the selection of the graphical indicia 304, the client training application 138 can cause a context for a task performed using the EHR to be captured as described above in the description of FIG. 1. For example, the context can include at least one of an identifier for a clinical activity, an identifier for a specific GUI element within the EHR, an identifier for the healthcare worker 104, and a job function of the healthcare worker 104. The client computing device 102 can then transmit the context to the second server computing device 120. After determining that the healthcare worker 104 and/or the healthcare organization of the healthcare worker 104 have access to the services of the training application 126, the training application 126 can transmit data to the client computing device 102 which causes a GUI for the client training application 138 to be presented on the client computing device 102.

Figure 4:
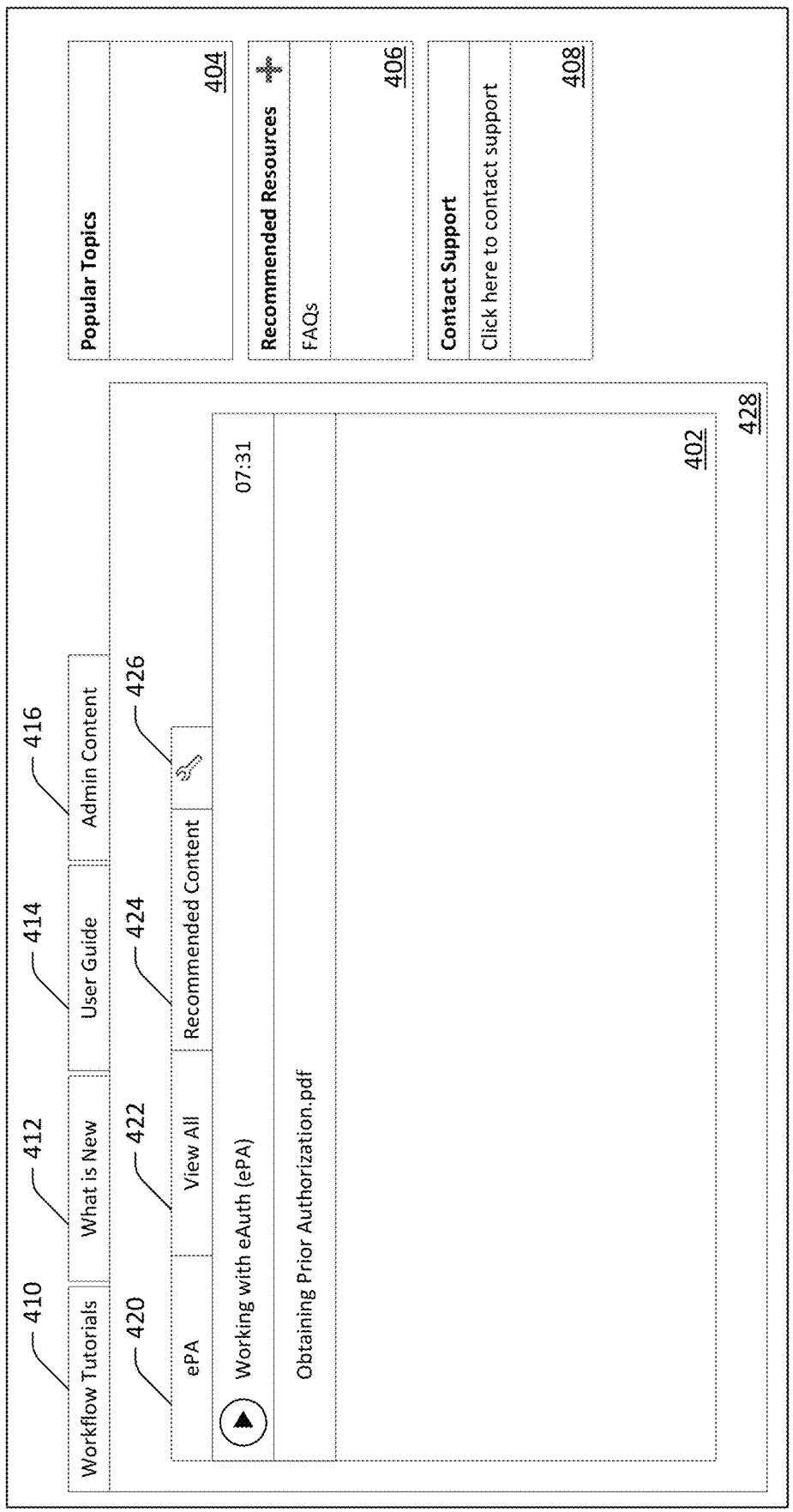
FIG. 4 is an exemplary GUI for presenting training material to a healthcare worker.

With reference to FIG. 4, an exemplary GUI 400 for the client training application 138 that can be presented on the display 140 of the client computing device 102 is depicted. When the healthcare worker 104 selects the graphical indicia 304 of the GUI 300 for the EHR, the GUI 400 is displayed, wherein in the embodiment shown in FIG. 4, the GUI 400 is displayed in a window separate from the GUI 300 of the client EHR. However, it is to be understood that in other embodiments, the GUI 300 of the client EHR and the GUI 400 of the training application 126 may be displayed simultaneously on a display of the client computing device 102 (e.g., the GUI 400 can be displayed as a popup window overlaying at least a portion of the GUI 300).

In the embodiment depicted in FIG. 4, the GUI 400 can include a plurality of outer selectable tabs 410-416 as well as a currently displayed field 428. When a user of the training application selects an outer selectable tab in the plurality of outer selectable tabs 410-416, the currently displayed field 428 can be populated with content referred to in the tab. In the embodiment depicted in FIG. 4, when the healthcare worker selects the workflow tutorials tab 410, the currently displayed field 428 can be updated to display selectable names of workflow tutorials. The GUI 400 can also include a new content tab 412. When the new content tab 412 is selected, the client computing device 102 can present names of training materials that have been recently added to the training application 126 (e.g., materials added to the training application 126 since a last time the healthcare worker 104 accessed the GUI of the client training application 138). Additionally, the GUI 400 can include a user guide tab 414. When the user guide tab 414 is selected, the client computing device 102 can present the user guide for the EHR within the GUI 400. The GUI 400 may also include an administrator content tab 416. It is contemplated that the administrator content tab 416 is not normally visible to the healthcare worker 104. Instead, the administrator content tab is displayed only when an administrator of the training application 126 is accessing the training application 126 (e.g., by way of a client training application). When the administrator content tab 416 is selected, a GUI for an administrator can be presented on the display 140 of the client computing device 102.

Depending on the tab selected, the currently displayed field 428 may also include a plurality of inner tabs 420-426. In the embodiment depicted in FIG. 4, an ePA (electronic prior authorization) tab 420 is depicted. When the ePA tab 420 is selected by the healthcare worker 104, the client computing device 102 can display selectable names of training materials relating to obtaining electronic prior authorization for a prescription medication for a patient (e.g., "Working with eAuth (ePA)" 401 and "Obtaining Prior Authorization.pdf" 402). The GUI 400 can also include a view all tab 422. When the view all tab 422 is selected by the healthcare worker 104, the client computing device 102 can display all training materials available to the healthcare worker 104. The GUI 400 can include a recommended content tab 424. Responsive to receipt of a selection of the recommended content tab 424, the client computing device 102 can display selectable names of training materials that are indicated in the training data 130 or the user data 131 as having been recommended to the healthcare worker 104 by a colleague (e.g., an administrator of the EHR, a supervisor of the healthcare worker, etc.). Additionally, the GUI 400 may include a configuration tab 426. When the configuration tab 426 is selected, the client computing device 102 can present the healthcare worker with options for configuring the GUI 400. In certain embodiments, the configuration tab 426 may only appear when an administrator of the training application 126 is accessing the training application 126 (e.g., by way of a client training application).

The GUI 400 can include a popular topics field 404. The popular topics field can display selectable names of training materials that have been accessed frequently by other users (e.g., other healthcare workers) of the training application 126. When a healthcare worker selects a training material in the popular topics field 404, the training material can be presented to the healthcare worker 104. Additionally, the GUI 400 can include a support field 406 which can display methods to contact individuals that support the training application 126. For example, the support field 406 can contain email addresses, telephone numbers, addresses, and other methods of communication.

Figure 5:
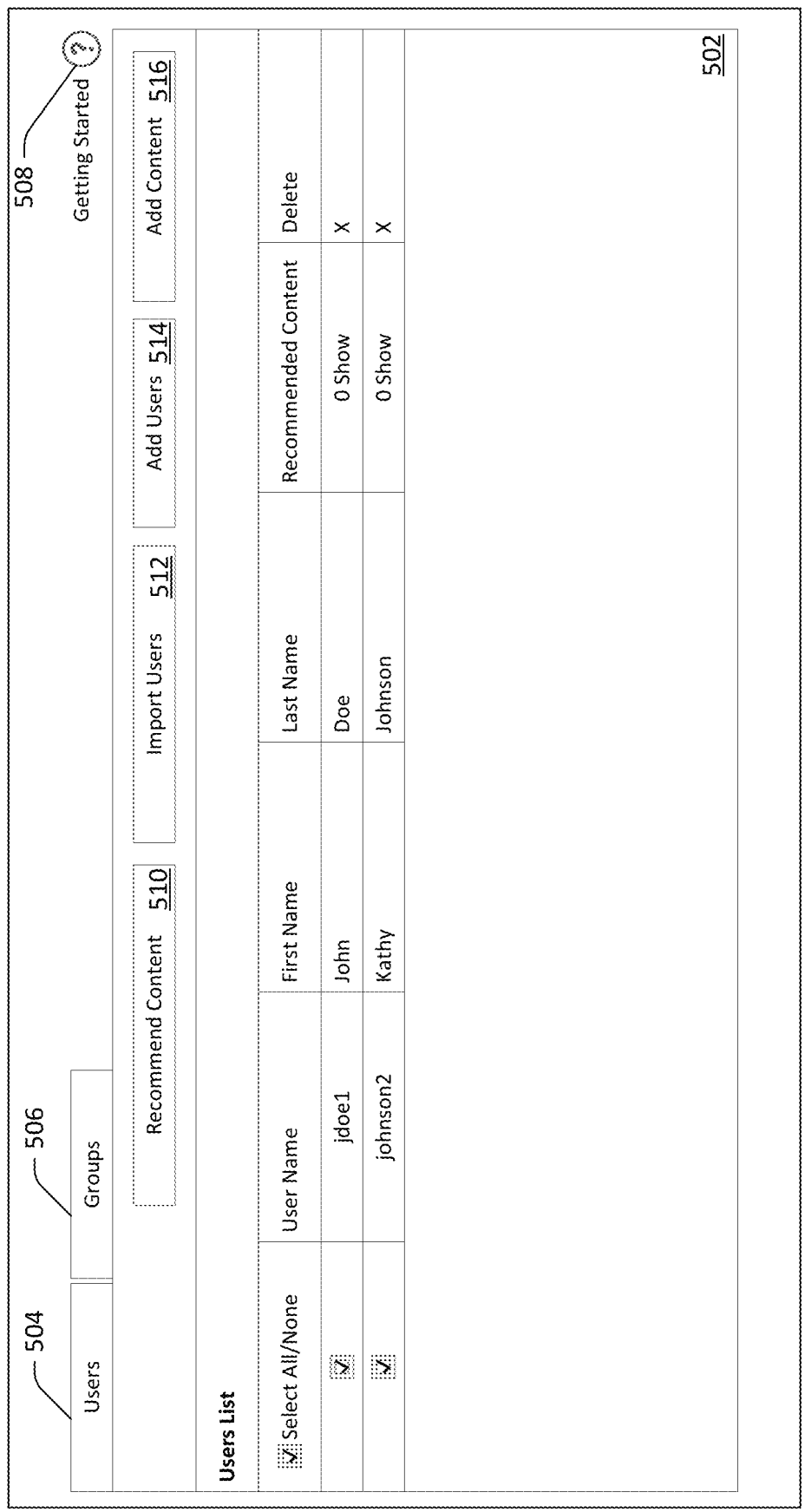
FIG. 5 is an exemplary GUI for an administrator.

Turning to FIG. 5, an exemplary GUI 500 for an administrator is depicted. It is contemplated that the administrator is an information technology worker (IT worker); however, the administrator may also be a supervisor of the healthcare worker or another employee belonging to the healthcare organization. When the administrator content tab 416 of the GUI 400 is selected, the GUI 500 is presented. The GUI 500 can include a plurality of selectable tabs 504-506. For example, the GUI 500 can include a users tab 504. When the user tab 504 is selected by the administrator, the GUI 500 can display a user list 502 comprising selectable names and personal details of current users (e.g., healthcare workers) of the training application 126. The GUI 500 may also include a groups tab 506. When the groups tab 506 is selected by the administrator, the administrator computing device can cause a plurality of different groups of users to be presented in the GUI 500. The groups tab 506 enables an administrator to easily group users sharing certain characteristics together. For example, the administrator can create a group consisting of healthcare workers in the same department, a group consisting of healthcare workers working in the same healthcare facility, etc. The GUI 500 can also include a selectable graphical indicium 508. When selected, the graphical indicia 508 can present instructions to the administrator on how to configure the training application 126.

The GUI 500 can include a recommend content button 510. The administrator can first select a first user in the users list 502. Then, when the recommend content button is selected by the administrator, a popup window can be displayed in the GUI 500. The popup window can include a list of training materials available to the training application 126. The training application 126 can receive input from the administrator indicating that a recommended training material in the list of training materials shown in the popup window has been selected. The training application 126 can store an indication of the recommended training material and the first user such that an identifier for the at least one training material will be presented to the first user the next time the first user selects the recommended content tab 424 of the GUI 400.

Additionally, the GUI 500 can include an import users button 512. When the import users button 512 is selected by the administrator, the training application 126 can present a prompt to the administrator prompting the administrator to upload at least one file containing at least one user. For example, the at least one file can be a comma separated value (CSV) file, a database file, a spreadsheet file, etc. The import users button 512 enables bulk loading of users to the training application 126. The GUI 500 further comprises an add users button 514, which enables the administrator to add an individual user. Furthermore, the GUI 500 can include an add content button 516, which when selected, can cause the GUI 500 to present the administrator with a prompt to select at least one training material stored on the administrator computing device (e.g., a newly created video for a new functionality added within the EHR). The training application 126 can then cause the training material to be stored in the data store 128 and to be made available to users of the training application 126.

Figure 6:
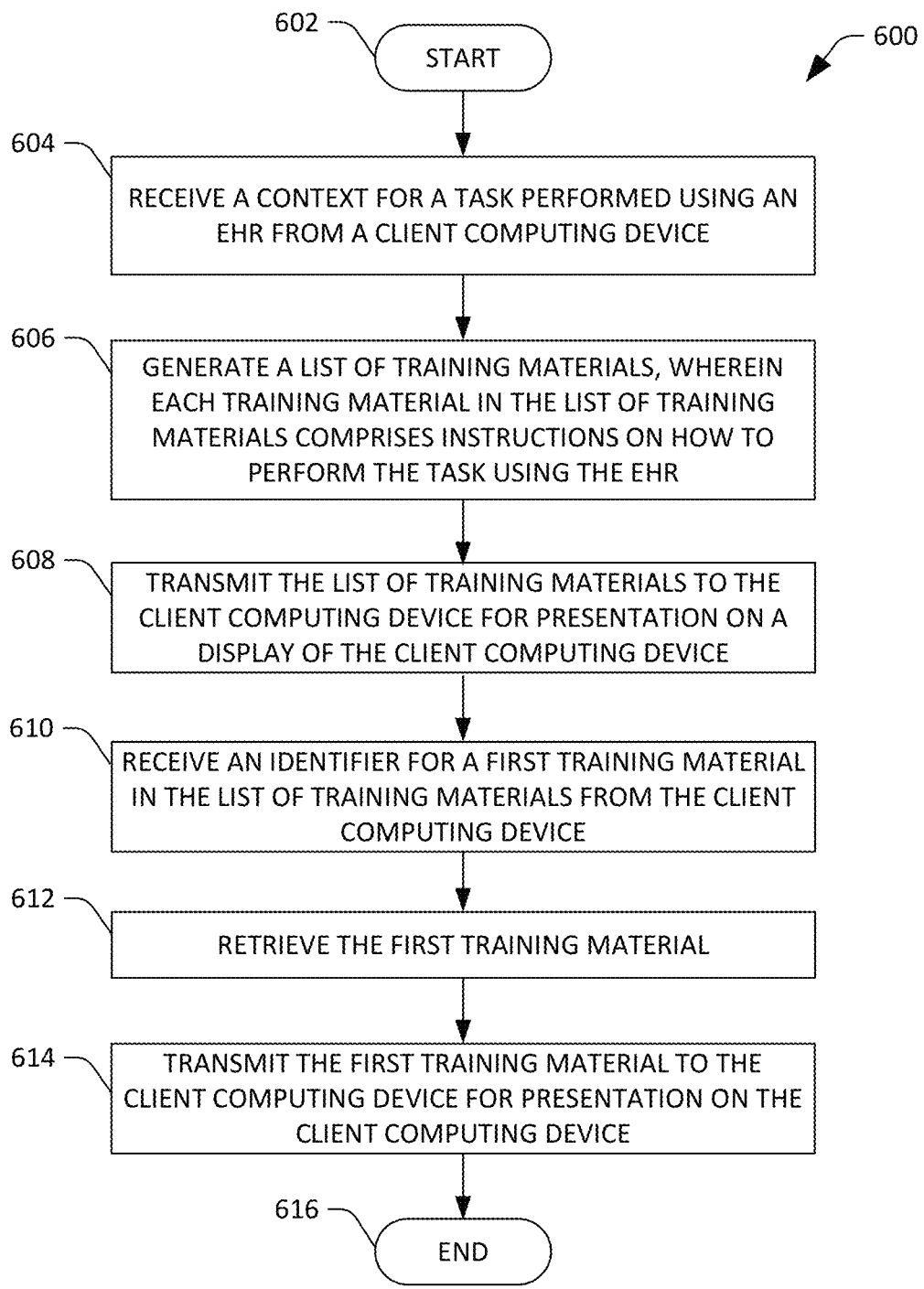
FIG. 6 is an exemplary methodology executed by a server computing device for presenting training material for a task performed using an EHR to a healthcare worker.
Figure 7:
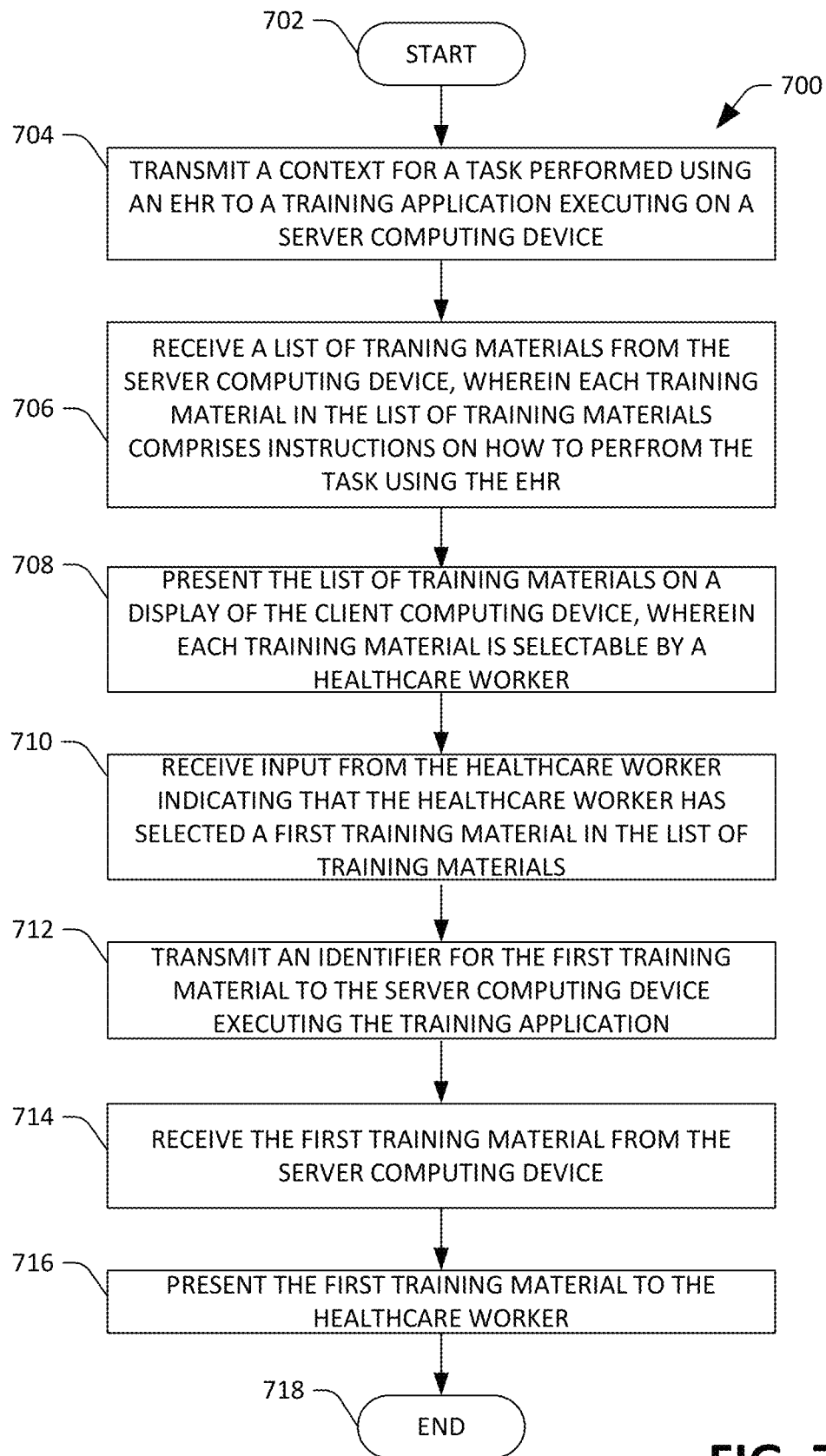
FIG. 7 is an exemplary methodology executed by a client computing device for presenting training material for a task performed using an EHR to a healthcare worker.

FIGS. 6-7 illustrate exemplary methodologies relating to presenting training data to a healthcare worker. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 6, a methodology 600 executed at a server computing device that facilitates presenting training data to a healthcare worker is illustrated. The methodology 600 begins at 602, and at 604 a context for a client EHR is received from the client EHR executing on a client computing device operated by a healthcare worker. As described above, the context can include at least one of an identifier for a clinical activity, data indicative of a task desirably performed by way of the EHR, an identifier for a specific GUI element within a client EHR, an identifier for the healthcare worker, and a job function of the healthcare worker. At 606, responsive to receiving the context from the client EHR, the server computing device generates a list of training materials by executing a search over training data based on the context. Each training material in the list of training materials comprises instructions on how to perform a respective task using the EHR. As detailed above, a training material may be a text-based document, a video file, an audio file, an interactive tutorial, etc. At 608, responsive to generating the list of training materials, the server computing device transmits the list of training materials to the client computing device for presentation on a display of the client computing device.

At 610, subsequent to transmitting the list of training materials to the client computing device, the server computing device receives an identifier for a first training material in the list of training materials from the client computing device. At 612, the server computing device transmits the first training material to the client computing device for presentation on the client computing device (e.g., upon retrieving the first training material from a datastore by executing a search over training data in the datastore based upon the identifier for the first training material). The methodology 600 concludes at 614.

With reference to FIG. 7, a methodology 700 executed at a client computing device that facilitates presenting training data to a healthcare worker is illustrated. The methodology 700 begins at 702, and at 704 the client computing device receives input from a healthcare worker which causes the client computing device to transmit a context for a client EHR executing on the client computing device to a training application executing on a server computing device. At 706, the client computing device receives a list of training materials from the training application executing on the server computing device. Each training material in the list of training materials comprises instructions on how to perform a respective task using the EHR. At 708, responsive to receiving the list of training materials, the client computing device presents an indication of each of one or more training materials in the list of training materials on a display of the client computing device. Each training material in the list of training materials is selectable by the healthcare worker.

At 710, subsequent to displaying the indications of the one or more training materials, the client computing device receives input from a healthcare worker indicating that a first training material in the one or more training materials has been selected by the healthcare worker. At 712, responsive to receiving the input from the healthcare worker, the client computing device transmits an identifier for the first training material to the server computing device. At 714, subsequent to transmitting the identifier for the first training material to the server computing device, the client computing device receives the first training material from the server computing device. At 716, the client computing device presents the first training material to the healthcare worker. The methodology 700 concludes at 718.

Figure 8:
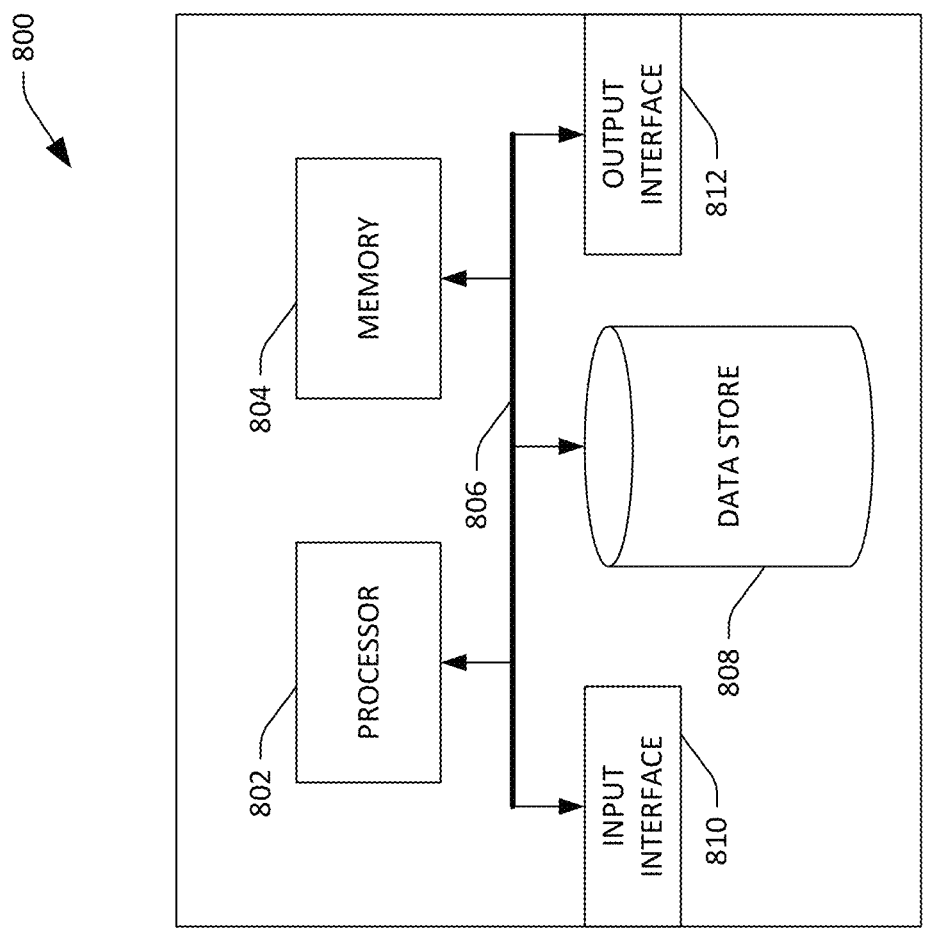
FIG. 8 is an exemplary computing system.

Referring now to FIG. 8, a high-level illustration of an exemplary computing device 800 that can be used in accordance with the systems and methodologies disclosed herein is illustrated. For instance, the computing device 800 may be used in a system that facilitates presenting training data for a task performed using an EHR. By way of another example, the computing device 800 can be used in a system that presents training data to a healthcare worker that has been recommended by a colleague of the healthcare worker, such as an IT worker or a supervisor. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store training data, user ratings for training data, etc.

The computing device 800 additionally includes a data store 808 that is accessible by the processor 802 by way of the system bus 806. The data store 808 may include executable instructions, training data, user ratings for training data, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A server computing device, comprising:
   a processor; and
   memory that has a training application loaded therein, wherein the training application, when executed by the processor, causes the processor to perform acts comprising:
      receiving, over a network connection, a context from an electronic health records application (EHR) executing on a client computing device operated by a healthcare worker, the context comprising data indicative of an identity or job function of the healthcare worker, a task desirably performed by way of the EHR, or an element of a GUI of the EHR being presented on a display of the client computing device;
      responsive to receiving the context from the EHR, generating a list of training materials by executing a search over training data stored in a computer-readable data store based on the context, wherein each training material in the list of training materials comprises instructions pertaining to performing a respective task using the EHR; and
      responsive to generating the list of training materials, transmitting, over the network connection, data to the client computing device that is configured to cause the client computing device to present a GUI for the training application on the display of the client computing device, wherein an identifier for a training material in the list of training materials is displayed in the GUI for the training application.

2. The server computing device of claim 1, wherein the data transmitted to the client computing device is configured to cause the GUI for the EHR and the GUI for the training application to be displayed simultaneously on the client computing device.

3. The server computing device of claim 1, the acts further comprising:
   prior to receiving the context from the EHR:
      receiving a notification from the client computing device that the healthcare worker has logged into the EHR;
      responsive to receiving the notification, determining whether the healthcare worker has permission to access the training application; and
      when the healthcare worker has permission to access the training application, causing a graphical indicium to be presented in the GUI for the EHR indicating that the healthcare worker has permission to access the training application.

4. The server computing device of claim 1, wherein each training material in the list of training materials has an associated rating, the acts further comprising:
   identifying a subset of training materials in the training data having a rating higher than a threshold value;
   wherein the data transmitted to the client computing device is further configured to cause an identifier for the subset of training materials to be displayed in a field in the GUI for the training application.

5. The server computing device of claim 1, the acts further comprising:
   prior to receiving the context from the EHR:
      receiving the training material in the list of training materials from a source; and
      responsive to receiving the training material, storing the training material in the computer-readable data store.

6. The server computing device of claim 1, the acts further comprising:
   receiving an identifier for a first training material in the list of training materials from the client computing device; and
   responsive to receiving the identifier for the first training material, transmitting the first training material to the client computing device for presentation on the display of the client computing device.

7. The server computing device of claim 6, the acts further comprising:
   subsequent to transmitting the first training material to the client computing device:
      receiving a rating for the first training material from the client computing device; and
      updating the training data with data indicating the rating for the first training material.

8. The server computing device of claim 7, wherein the first training material is a text-based file, a video file, or an audio file.

9. The server computing device of claim 1, the acts further comprising:
receiving an identifier for a recommended training material from an administrator computing device; and
responsive to receiving the identifier for the recommended training material, transmitting the identifier for the recommended training material to the client computing device for presentation on the display of the client computing device.

10. The server computing device of claim 9, the acts further comprising:
receiving a first notification from the client computing device that the recommended training material has been presented to the healthcare worker; and
forwarding the first notification to the administrator computing device.

11. A method executed by a server computing device comprising:
receiving, over a network connection, a context from an electronic health records application (EHR) executing on a client computing device operated by a healthcare worker, the context comprising data indicative of an identity or job function of the healthcare worker, a task desirably performed by way of the EHR, or an element of a GUI of the EHR being presented on a display of the client computing device;
responsive to receiving the context from the EHR, generating a list of training materials by executing a search over training data stored in a computer-readable data store based on the context, wherein each training material in the list of training materials contains instructions pertaining to performance of a respective task using the EHR;
responsive to generating the list of training materials, transmitting, over the network connection, the list of training materials to the client computing device for presentation on the display of the client computing device, wherein the list of training materials is presented on the display;
subsequent to transmitting the list of training materials to the client computing device, receiving, over the network connection, an identifier for a first training material in the list of training materials from the client computing device;
responsive to receiving the identifier for the first training material, transmitting, over the network connection the first training material to the client computing device for presentation on the display of the client computing device, wherein the first training material is presented on the display.

12. The method of claim 11, wherein the first training material is a text-based file, a video file, or an audio file.

13. The method of claim 11 further comprising:
prior to receiving the context from the EHR:
receiving the first training material from a source; and
responsive to receiving the first training material, storing the first training material in the computer-readable data store.

14. The method of claim 11 further comprising:
receiving an identifier for a recommended training material from an administrator computing device; and
responsive to receiving the identifier for the recommended training material, transmitting the identifier for the recommended training material to the client computing device for presentation on the display of the client computing device.

15. The method of claim 14 further comprising:
receiving a first notification from the client computing device that the recommended training material has been presented to the healthcare worker; and
forwarding the first notification to the administrator computing device.

16. A computer-readable storage medium comprising instructions that, when executed by a processor of a server computing device, cause the processor to perform acts comprising:
detecting a first application programming interface (API) call generated by a client computing device over a network connection, wherein the first API call comprises a context for an electronic health records application (EHR) executing on the client computing device, the context comprising data indicative of at least one of an identity or job function of the healthcare worker, a task desirably performed by way of the EHR, or an element of a GUI of the EHR being presented on a display of the client computing device;
responsive to detecting the first API call, generating a list of training materials by executing a first search over training data stored in a computer-readable data store based on the context, the training data comprising a plurality of training materials pertaining to the EHR, wherein each training material in the training data comprises instructions on how to perform a respective task using the EHR;
responsive to generating the list of training materials, transmitting, over the network connection, data to the client computing device that is configured to cause the client computing device to present a GUI for a training application on the display of the client computing device, wherein an identifier for each training material in the list of training materials is displayed in the GUI for the training application.

17. The computer-readable storage medium of claim 16, the acts further comprising:
detecting a second API call generated by the client computing device, wherein the second API call comprises an identifier for a first training material in the list of training materials;
responsive to detecting the second API call, retrieving the first training material by executing a second search over the training data based on the identifier for the first training material; and
transmitting the first training material to the client computing device for presentation on the client computing device.

18. The computer-readable storage medium of claim 17, wherein the first API call is a first HTTP/s request and the second API call is a second HTTP/s request, and wherein detecting the first API call comprises monitoring a first port for the first HTTP/s request, and wherein detecting the second API call comprises monitoring a second port for the second HTTP/s request.

19. The computer-readable storage medium of claim 17, wherein the first training material is a text-based file, a video file, or an audio file.

20. The computer-readable storage medium of claim 16, wherein each training material in the training data has an associated upload datetime, wherein the first API call further comprises a first datetime, the acts further comprising:
recording the first datetime;
receiving an indication from the client computing device indicating that the healthcare worker has exited the GUI for the training application;

subsequent to receiving the indication, detecting a second API call generated by the client computing device, wherein the second API call comprises the context and a second datetime;

responsive to detecting the second API call, generating a second list of training materials by executing a second search over the training data based on the context and the second datetime, wherein the associated upload datetime of each training material in the second list of training materials is after the first datetime; and displaying the second list of training materials in a field in the GUI for the training application.

\* \* \* \* \*